United States Patent [19]

Karpas

[11] Patent Number: 4,814,269

[45] Date of Patent: Mar. 21, 1989

[54] DIAGNOSTIC TESTING FOR ANTIBODIES AGAINST MICROORGANISMS

[75] Inventor: Abraham Karpas, Cambridge, Great Britain

[73] Assignee: Cenfold Holdings S.A., Panama City, Panama

[21] Appl. No.: 842,228

[22] Filed: Mar. 21, 1986

[30] Foreign Application Priority Data

Mar. 29, 1985 [GB] United Kingdom ............... 8508274
Aug. 30, 1985 [GB] United Kingdom ............... 8521684

[51] Int. Cl.⁴ .............. G01N 33/554; G01N 33/569; G01N 33/571; G01N 33/574
[52] U.S. Cl. .......................... 435/5; 435/7; 435/820; 435/948; 436/510; 436/519; 436/809; 436/813
[58] Field of Search ............ 435/5, 7, 810, 820, 435/948; 436/519, 813, 809, 510; 422/99

[56] References Cited

U.S. PATENT DOCUMENTS

| | | | |
|---|---|---|---|
| 4,520,113 | 5/1985 | Gallo et al. | 435/7 |
| 4,588,681 | 5/1986 | Sawada et al. | 435/5 |
| 4,607,008 | 8/1986 | Coates et al. | 435/7 |

FOREIGN PATENT DOCUMENTS

WO83/00877 3/1983 PCT Int'l Appl.
2098730 11/1982 United Kingdom.

OTHER PUBLICATIONS

Dal Conte et al, *Journ. of Infection*, 16, 263–272, 1988.
Karpas et al, *The Lancet*, Jul. 18, 1987, pp. 132–133.
Werner et al, *The Lancet*, Nov. 9, 1985, p. 1065.
M. Naiem et al, *Journ. Immunol. Meth.*, 50, 145–160, 1982.
G. Gerna, in G. Feldmann et al (Eds.), *Immunoenzymatic Techniques*, North-Holland Publishing Co., Amsterdam, 1976, pp. 443–449.
D. Y. Mason et al, in G. R. Bullock et al (Eds.), *Techniques in Immunocytochemistry*, Academic Press, New York, 1983, pp. 175–195.
M. Naiem et al, *Biol. Abstr.*, 75, Abstr. No. 41879, 1983.
Kuhlman, W. D., "Immuno Enzyme Techniques in Cytochemistry," 1st Edition, pp. 61–67, Verlag Chemie, Basel, CH; 1984.
Popovic et al., M., "Detection, Isolation and Continuous Production of Cytopathic Retroviruses (HTLV-III) from Patients with AIDS and Pre-AIDS," *Science* 224, pp. 497–500, May 4, 1984, Washington, U.S.

*Primary Examiner*—Sam Rosen
*Assistant Examiner*—David A. Saunders
*Attorney, Agent, or Firm*—Robbins & Laramie

[57] ABSTRACT

A method of testing a fluid sample for the presence of antibodies against a micro-organism, which comprises contacting the sample with fixed cells or fragments of cells infected with the micro-organism, and determining the presence of antibody bound to the cell-associated antigens, in which the determination is by virtue of a color change visible to the naked-eye at the site of the antibodies. For use in a testing method of this type, a test component comprises upper and lower layers, in which the upper layer has an array of apertures through which discrete areas on the lower layer are exposed, and in which the lower layer carries, in some at least of the discrete areas, fixed cells or cell fragments infected by a micro-organism.

6 Claims, No Drawings

DIAGNOSTIC TESTING FOR ANTIBODIES AGAINST MICROORGANISMS

FIELD OF THE INVENTION

This invention relates to diagnostic testing. In particular, it concerns a diagnostic test for microorganisms, and especially for viral infections, based on detection of antibodies to a given virus in biological samples such as blood plasma or serum, and also a product for use in such a test. The invention finds particular application in testing for the virus which causes acquired immune deficiency syndrome (AIDS), e.g. lymphadenopathy-associated virus (LAV), but is also applicable to testing for adult T-cell leukemia (ATLV/HTLV). LAV is widely (and possibly incorrectly) referred to as HTLV-III.

BACKGROUND OF THE INVENTION

Tests are known for detecting the presence in blood samples of antibodies to microorganisms including viruses such as AIDS and ATLV/HTLV. The known tests use purified or partially purified inactivated virus or antigens as the basis for an immunoassay procedure, e.g. using an enzyme-linked immunosorbent assay (ELISA) technique. There is, for example, the Organon-Teknika indirect ELISA ("Vironostika" anti-HTLV-III).

In such assays, test wells in a plastics test plate are coated with the purified or partially purified virus, and samples to be tested are then added to the wells. Any antibody to LAV or another microorganism such as ATLV/HTLV will bind to the virus, and the presence of bound antibody is then determined by adding a second labelled antibody which selectively binds to the first antibody. The antibody label is then detected in suitable manner, e.g. by adding a substrate which changes color in the presence of an enzyme label. The color change is indicative of the presence of the antibody in the sample.

The restricted mode of transmission of the AIDS virus should enable effective screening of carriers, to check the spread of the virus in a population. However, the known tests are found not to be completely reliable; they tend to give an unacceptably high rate of false positive, and also negative, results. One possible reason for inaccuracy is impurity of the virus and contamination with other antigens with which antibodies in the sample will bind. Unspecific "stickiness" of the plastics material of the test plate may also cause unwanted binding of reagents.

Popovic et al, Science 224 (4 May 1984) 497–500 (and also Example 3 of U.S. Pat. No. 4,520,113), describe the detection of viruses in patients with AIDS, by the following test: cells were infected with HTLV-III and spotted on slides, human serum was added to the slides, the slides were washed and then reacted with fluorescein-conjugated goat anti-human IgG before being rewashed and examined for fluorescence under a microscope. In a control, uninfected cells were used.

Karpas, Mol. Biol. Med. 1 (1983) 457–459, had previously disclosed screening, by immunofluorescence, for the presence of antibodies in the sera of homosexuals with or without AIDS, using acetone-fixed cells. The important conclusion of Karpas's disclosure was that the sera did not have antibodies to ALV (HTLV), and that another virus might be involved in the development of AIDS.

It would be very desirable to provide a cheaper and more convenient test for AIDS than immunofluorescence, while minimizing or avoiding the occurrence of false positive reactions.

SUMMARY OF THE INVENTION

According to one aspect of the present invention, a method of testing a fluid sample for the presence of antibodies, e.g. to AIDS virus or to adult T-cell leukaemia, comprises contacting the sample with cells or fragments of cells which have been infected with a microorganisms, e.g. the relevant virus, and determining the presence of antibody bound to the cell-associated antigens by a visible color change at the site of the antibodies.

According to another aspect of the present invention, a test component comprises two layers; an upper layer has an array of apertures through which discrete areas of the lower layer are exposed, and the lower layer carriers, in at least some of the discrete areas, fixed cells or cell fragments infected with a microorganism.

DETAILED DESCRIPTION OF THE INVENTION

The invention uses a cell which is infectable with the microorganisms or virus in question. It is preferred to use a human T-cell line in the case of ATLV/HTLV, but other human or animal (e.g. monkey) cell lines might also be used. The human T-cell line known as Karpas 45 or Karpas T-cells is particularly preferred for testing for AIDS antibodies, because cells from this line infected with AIDS virus express a very large amount of viral antigens. Details of this cell line are given by Karpas et al, Leukemia Research 1 (1977). However, other cell lines which are infectable by the AIDS virus or other microorganism could be used.

When practicing the invention, cells from a given cell line are infected with the relevant virus which replicates, producing infected cells. Any antibodies to the virus in a sample added to the cells will selectively bind to the viral antigen. The presence of bound antibody is then determined colorimetrically. For example, suitably labelled antibodies to the bound antibody or Staphylococcus A protein can be added, and these will selectively bind to the bound antibody to be detected. Following the addition of a substrate, detection can be by the naked eye; detection of the label indicates the presence of the antibody in question, and the absence of label indicates the absence of the antibody to be detected.

In order to control the specificity of the reaction, it may be desirable also to use uninfected cells from the same cell line, in identical manner to the infected cells, to provide a reference standard. Any anti-cellular antibodies in the cells will react in a similar way with both infected and uninfected samples. The effect of such anti-cellular antibodies can accordingly be monitored and taken into consideration, if appropriate, using a bench microscope for confirmation of results seen by the naked eye.

The invention is conveniently carried out using cells fixed to a suitable carrier, e.g. in the form of a sample slide or located in test wells on a test plate. The carrier may be of any suitable material which is unaffected by the reagents used. Since the desired reactions involve a color change, the carrier material is preferably transparent or white. Glass is one particularly suitable material for this purpose, being transparent, inert, cheap and readily available.

The uses and functions of a glass slide and a multi-well plate are combined in a test component of the invention. The cells are immobilized on one surface on the slide, and are exposed in discrete areas through an upper layer having a plurality of apertures; the slide and the upper layer form the two-layer component. The apertured layer is suitably of a plastics material, e.g. Teflon (registered Trade Mark), and may be very thin, i.e. its function is then merely to define the discrete areas on the carrier layer, and will then preferably have a contrasting appearance, e.g. white as opposed to a transparent slide.

A test component for use in the invention defines an array of discrete, spaced test areas, e.g. in a 3×5 or 8×12 matrix. In such an embodiment, it may be convenient to locate infected cells in all or only some of the areas, e.g. only in one or more selected rows or columns, with uninfected cells located in the remaining areas for reference purposes as noted above. A relatively large plate which carries infected cells in all areas (8×12), may be used for primary screening. If any check on positive reactions is required, that can be done using a relatively small plate carrying an array of infected and uninfected cells (3×5). For true comparison, the infected and uninfected cells should of course be from the same cell line.

When preparing a carrier for use, cells (infected or uninfected as appropriate) are located thereon, e.g. on a glass carrier. The cells are air-dried and then fixed using a suitable fixative which functions both to kill the virus in the infected cells and to make the cells permeable to antibodies without destroying the viral antigens. Acetone is one suitable fixative, but other reagents can also be used.

When carrying out the invention, a small quantity of sample fluid to be tested, e.g. blood (serum or plasma) or other body fluid, is added to the fixed cells. The samples are then incubated for a suitable time at a suitable temperature (from 0 to 50 C.). Incubation time depends on the temperature: for example, at 37 C., incubation of about 1 hour could be sufficient, whereas at 0 C. incubation times of 5 or more hours might be required. After incubation, the sample carrier, e.g. slide, is washed in a suitable solution such as physiological saline, to remove any unbound antibodies, leaving only those antibodies which are chemically bound to the viral antigens.

The presence of the bound antibodies is then detected by a suitable colorimetric immunoassay procedure. For example, suitably labelled anti-human antibodies to the bound antibodies may be added. Alternatively, a suitably labelled Staphylococcus A protein may be used: such reagents bind to human IgG antibodies and so will give satisfactory results in most cases. The marker label most commonly used is horseradish peroxidase, but alkaline phosphatase or colloidal gold might also be used.

After incubation, any unbound marker material is then washed off, and suitable steps are then taken to visualize the bound marker labels, if necessary. For example, where the marker is horseradish peroxidase, a suitable reagent such as aminoethylcarbazole is used to "develop" a red/brown color in the presence of the label. The intensity of the color developed is indicative of the amount of bound antibody from the sample being tested.

Because visible color changes are developed, the results can be inspected with the naked eye. A bench microscope need be used only to verify the specificity of staining, as required. Further, as may be required, the developed color of the label can be compared with results obtained from similar treatment of uninfected cells, which provide a reference standard.

A kit of the invention comprises a test component and conveniently also includes a supply of labelled antibodies to human immunoglobulin or labelled Staphylococcus A, and possibly also a supply of reagent for developing the label, if appropriate.

The invention finds particular applicability in testing for antibodies to viruses and has been found to give good, reliable and accurate results. The special value of the invention lies in its combination of rapid testing and the ability to read positive and negative results with the naked eye, more effectively than before, owing to the discovery that the use of infected cells reduces or eliminates false positive or negative readings. In conentional enzyme-linked immunosorbent assays, color changes are detected in the fluid; in use of the present invention, a precipitate is formed at the site of the antibodies. Indeed, the test component can be dried and stored before determination. These features are of enormous technical and commercial importance.

One preferred embodiment of the invention for testing for antibodies to AIDS virus will now be described, by way of example.

Cells from the Karpas T cell line are infected with AIDS virus. The resulting infected cells are fixed to selected test wells in a glass slide having a 3×5 array of wells; for example, infected cells are located in only two selected rows of the array. Uninfected cells from the same cell line are fixed to the remaining wells of the slide, for example in the remaining row of the array.

Following air-drying of the slide, the cells are fixed by the addition of acetone which acts to kill the virus and also to make the cells permeable to antibodies, without destroying the viral antigens.

Small samples of body fluid to be tested, such as blood plasma or serum, are added to each of the test wells and are incubated for a suitable time at a suitable temperature, for example for one hour at 37 C. or for 12 or more hours at 4 C. The slide is then washed with physiological saline to remove any unbound antibody.

Anti-human antibody to the human immunoglobulin, or Staph-A protein, labelled with horseradish peroxidase, is then added to the wells and incubated. Any unbound antibody is washed off, and the bound antibody is then "developed" by the addition of a substrate such as aminoethylcarbazole which produces a red/brown color in the presence of the peroxidase label. Other substrates can also be used. The intensity of the color developed provides an indication of the amount of bound AIDS antibody from the sample in question. If no color develops, that usually means that the material in question does not contain antibodies to the antigen in question. Negative sera can thus be monitored with the naked eye.

By contrast with color development in infected cell areas, the behaviour of the uninfected cell areas provides a reference standard with which the results from the infected areas can be compared. The results can be inspected either with the naked eye or under a microscope if more accurate information is required.

The following specific Example illustrates the invention. The following abbreviations are used:
PBS: phosphate-buffered saline
HRP: horseradish peroxidase
IP: immunoperoxidase
IF: immunofluorescence
CRIA: competitive radio-immunoassay
C-LAV: Cambridge isolate of LAV

EXAMPLE

Approximately $10^5$ cells were placed in each well of a multi-well slide, air-dried, and fixed for 10 min in acetone at room temperature. The slides contained three rows of wells. A drop of the test serum or plasma sample diluted 1 in 10 in saline or PBS was placed in each of two rows of wells which contain virus-infected cells and in one row of wells which contains non-infected cells. The preparation was incubated in a humidified chamber for at least 60 min at 37 C., then washed for 10 min in saline or PBS. A suspension of antibodies to human immunoglobulin tagged with HRP was then added.

A parallel set of slides was treated with similar goat antibodies tagged with fluorescein. Thus, each serum/plasma sample was tested for antibodies in duplicate and by two methods. Each also included a control.

Incubation in a humidified chamber was repeated and followed by washing for 10 min in saline or PBS. Fluorescein-stained preparations were examined with a fluorescence microscope while HRP-treated cells were stained with aminoethylcarbazole or equivalent substrates. The results of the IP reaction could be clearly distinguished by the naked eye and verified by examination under conventional low-power microscopy.

IP and IF results were the same. IP is cheaper and therefore preferred.

The results of comparative serological screening are tabulated below. 190 sera from both Addenbrooke's Hospital, Cambridge, and Westminster Hospital, London, were tested independently both by the IP test described above and by the Public Health Laboratory Service, London, using the CRIA described by Mortimer et al, British Med. J. 290 (1985) 1176-79. The latter gave a high rate (12/190) of ambiguous readings, whereas the IP test gave clear and unambiguous results.

|         |   | CRIA |     |    |
|---------|---|------|-----|----|
|         |   | +    | −   | ±  |
| IP test | + | 47   | 3   | 7  |
|         | − | 0    | 128 | 5  |

C-LAV (see Karpas, Mol. Biol. Med. 1 (1983) 457, and also The Lancet 2 (1985) 695), unlike other viral isolates in other human T-cell lines, causes a complete cytolysis of the Karpas T-cells. However, since the relevant T-cell line grows very well in vitro to give practically unlimited quantities, a continuous supply of virus-infected cells can be generated. However, the lytic effect makes it possible to test for neutralizing antibodies.

In one study, Karpas T-cells were infected with a serum/virus mixture obtained after 1 h. incubation of 0.1 ml of serum samples with $10^4$ infectious C-LAV particles. Nine sera were tested. Two sera from AIDS patients did not block the lytic effect of the virus, whereas five out of seven sera from healthy antibody-positive homosexuals blocked the lytic effect for over 10 days.

The high levels of viral antigen which accumulate in the cells make it possible to monitor the results of IP staining with the naked eye. The incorporation in the test slides of wells with virus-negative cells allows the specificity of the reaction for each serum sample to be controlled separately. This ability to discriminate between anti-viral and anti-cellular antibodies is very important in the case of homosexuals and recipients of blood transfusions, who commonly have some anti-cellular antibodies.

The detection of positive reactions with the naked eye and confirmation with microscopy allows the elimination of the false readings associated with radio-activity or ELISA counters. No specialized expertise is required, nor any sophisicated equipment; a refrigerator and a conventional microscope are all that are needed. Any questionable result can easily be repeated, and in the unlikely event that IP remains questionable, similar slides can also be used in IF tests. The acetone fixation of the slides kills the virus and consequently the slides are entirely safe to handle. Slides which had been stored at +4 C. for over three months have been used satisfactorily.

The method of the invention is a reliable and safe test, easy to perform. It provide a simple and inexpensive method for large-scale screening of blood for anti-LAV antibodies and can give accurate results within 2 h. Moreover, positive sera can be further monitored for neutralizing antibodies to the virus with the simple procedure described above; thus, sera with high titres of neutralizing antibodies can be selected for possible immunotherapy trials in AIDS patients.

We claim:

1. A method of testing a fluid sample for the presence of polyclonal antibodies against a microorganism comprising infecting cells of the Karpas human T-cell line with said microorganism, fixing the infected cells or infected cell fragments, contacting the fixed infected cells or fixed infected cell fragments with a fluid sample, and then determining the presence of antibodies bound to the fixed cells or fixed cell fragments associated antigens of the microorganism, said determination being confirmed by a color change visible to the naked eye at the site of the antibodies on the fixed cells or fixed cell fragments.

2. The method of claim 1 wherein the sample is also contacted with uninfected fixed cells or fixed cell fragments of the Karpas human T-cell line, for reference during the determination.

3. The method of claim 1 wherein the microorganism is a virus.

4. The method of claim 3 wherein the virus is the AIDS virus or the adult T-cell leukemia virus.

5. The method of claim 1 wherein the sample is contacted with a test component comprising upper and lower layers, in which the upper layer has an array of apertures through which discrete areas on the lower layer are exposed, and in which the lower layer carries, in at least some of the discrete areas, fixed cells or fixed cell fragments infected by a microorganism.

6. The method of claim 2 wherein the sample is contacted with a test component comprising upper and lower layers in which the upper layer has an array of apertures through which discrete areas on the lower layer are exposed, and in which the lower layer carries, in the discrete areas, fixed cells or fixed cell fragments, some of which are uninfected and others of which are infected by a microorganism.

* * * * *